Nov. 20, 1962 E. S. BOERNER Plant Pat. 2,195
ROSE PLANT
Filed Jan. 12, 1962
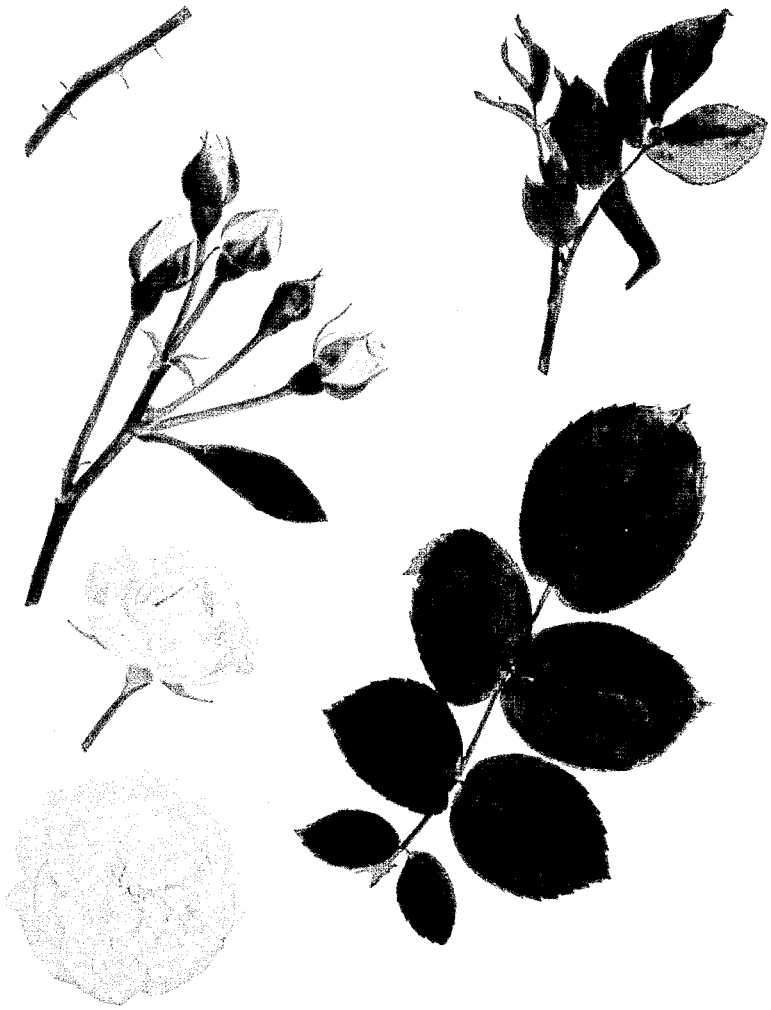
Inventor.
E. S. Boerner
By: Robb & Robb
Attorneys.

United States Patent Office

Plant Pat. 2,195
Patented Nov. 20, 1962

2,195
ROSE PLANT

Eugene S. Boerner, Newark, N.Y., assignor to Jackson & Perkins Company, Newark, N.Y., a corporation of New York Filed Jan. 12, 1962, Ser. No. 165,979
1 Claim. (Cl. 47—61)

The present invention relates to a new and distinct variety of rose plant of the floribunda class, which was originated by me by crossing an unnamed and unpatented seedling of "Lavender Pinocchio" (Plant Patent No. 947) with another unnamed hybrid tea seedling which is characterized by its dark red flowers.

The primary objective of this breeding was to produce a new rose variety of the floribunda class, in which hardiness is combined with deeper lavender colored flowers than any heretofore available in varieties of this class. This objective was fully achieved, along with other desirable features, as evidenced by the following unique combination of characteristics which are outstanding in the new variety and which distinguish it from its parents, as well as from all other varieties of which I am aware:

(1) Dwarf plant size;
(2) Good hardiness;
(3) A very free blooming habit throughout the entire growing season; and
(4) A distinctive and attractive Pale Rhodonite Pink general color tonality of the flowers.

Asexual reproduction of my new variety by budding, as performed at Newark, New York, and also at Pleasanton, California, shows that the aforementioned characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new varieyt, with color terminology in accordance with Ridgway's Color Standards and Nomenclature:

Parentage: Seedling.
*Seed parent.*—An unnamed seedling of "Lavender Pinocchio."
*Pollen parent.*—An unnamed dark red hybrid tea seedling.

Classification:
*Botanic.*—Floribunda
*Commercial.*—Floribunda.

*Flower*

(Observations made from specimens grown outdoors at Newark, New York, in the early morning during the latter part of the month of June.)

Blooming habit: Recurrent—continuous.

Bud:
*Size.*—Medium.
*Form.*—Ovoid; is not affected by wet or hot weather.
*Color.*—When sepals first divide—Vinaceous-Lilac, Plate 44. When petals begin to unfurl—Pale Vinaceous-Lilac, Plate 44. When half-blown: inside of petals—Rhodonite Pink, Plate 38, very lightly overcast with Pale Rhodonite Pink, Plate 38; reverse of petals—Pale Rose-Purple, Plate 26, lightly overcast with Pale Rhodonite Pink, Plate 38.
*Sepals.*—Smooth edge; curl back when petals begin to unfurl. Color: inside—Turtle Green, Plate 32; outside—Grass Green, Plate 6.

*Calyx.*—Color—Grass Green, Plate 6. Shape—pear. Size—long. Aspect—smooth. Odor when rubbed—none.
*Peduncle.* — Length — medium. Aspect — smooth. Strength — erect; slender. Color — Oil Green, Plate 5.
*Opening.*—Opens up well; is not affected by adverse weather conditions.

Bloom:
*Size.*—Small. Average size when fully expanded—2 inches.
*Borne.*—Both singly and several together; very free.
*Stems.*—Short; strong.
*Form (when first open).*—Cupped. Permanence—retains its form to the end, but flattens and outer petals curl back.
*Petalage.*—Double (full but open center). Number of petals under normal conditions—from 30 to 35.
*Color.*—Center of flower—Pale Laelia Pink, Plate 38, very lightly overcast with Pale Rhodonite Pink, Plate 38. Outer petals—Pale Rhodonite Pink, Plate 38, lightly overcast with Rosolane Pink, Plate 26. Base of petals (aiglet)—Primuline Yellow, Plate 16. Inside of petals—Pale Rhodonite Pink, Plate 38. Reverse of petals—Pale Purplish Vinaceous, Plate 39, lightly overcast with Rosolane Pink, Plate 26. General tonality from a distance—Pale Rhodonite Pink, Plate 38.
*Discoloration*—General tonality at end of first day—Pale Rhodonite Pink, Plate 38. Second day—Pale Rhodonite Pink, Plate 38. Third day—Pale Rhodonite Pink, Plate 38, lightly overcast with Rosolane Pink, Plate 26.

Petals:
*Texture.*—Thick; is not affected by wet or hot weather.
*Appearance.*—Inside—satiny. Outside—shiny.
*Form.*—Oval.
*Arrangement.* — Imbricated (regularly arranged shingle-like).
*Petaloids in center.*—Few; small.
*Persistence.*—Drop off cleanly.
*Fragrance.*—Moderate. Nature—tea (average hybrid tea scent).
*Lasting quality.* — On the plant — long. As cut flower—long.

*Genital Organs*

Stamens, anthers: Medium size; many; regularly arranged around styles. Color—Amber Yellow, Plate 16.
Stamens, filaments (threads): Medium length. Color—Naphthalene Yellow, Plate 16.
Pollen: Color—Massicot Yellow, Plate 16.
Styles: Bunched; even; medium length; thin.
Stigmas: Color—Primrose Yellow, Plate 30.
Ovaries: All enclosed in calyx.
Hips: None.
Seeds: None.

*Plant*

Form: Bush.
Growth: Vigorous; dwarf.
Foliage: Compound of 5–7 leaflets.
*Size.* Medium.
*Quantity.*—Normal.
*Color.*—New foliage: upper side—Spinach Green, Plate 5, with serrations of Oxblood Red, Plate 1; under side—Lettuce Green, Plate 5. Old foilage: upper side—Empire Green, Plate 32; under side—Bice Green, Plate 17.
*Shape.*—Oval pointed.

*Texture.*—Upper side—leathery. Under side—smooth.

*Ribs and veins.*—Ordinary.

*Edge.*—Smooth.

*Serration.*—Both double and single; small.

*Leaf stem.*—Color—Elm Green, Plate 17. Under side—smooth.

*Stipules.*—Short; smooth.

Wood:

*New wood.*—Color—Oil Green, Plate 5. Bark—smooth.

*Old wood.*—Color—Forest Green, Plate 17. Bark—smooth.

Thorns:

*Thorns.*—Quantity: onmain stalks from base—ordinary; on laterals from stalk—ordinary. Form— narrow base; short; straight. Color (when young) — Acajou Red, Plate 13. Position — irregular.

*Prickles.*—Quantity: on main stalks—none; on laterals—none.

*Short needles.*—Quantity: on main stalks—none; on laterals—none.

I claim:

A new and distinct variety of rose plant of the floribunda class, substantially as herein shown and described, characterized particularly as to novelty by the unique combination of a dwarf plant size, good hardiness, a very free-blooming habit, and a distinctive and attractive Pale Rhodonite Pink general tonality of the flowers.

No references cited.